United States Patent [19]

Gesteland

[11] 4,388,272
[45] Jun. 14, 1983

[54] METHOD AND APPARATUS FOR PRECISE CONTROL OF VAPOR PHASE CONCENTRATIONS OF VOLATILE ORGANICS

[75] Inventor: Robert C. Gesteland, Evanston, Ill.

[73] Assignee: Northwestern University, Evanston, Ill.

[21] Appl. No.: 252,039

[22] Filed: Apr. 8, 1981

[51] Int. Cl.³ .......................... B01L 5/00; C09K 3/00; G01N 1/22; A61L 9/04
[52] U.S. Cl. ...................................... 422/102; 53/79; 53/97; 73/1 G; 73/19; 73/23; 252/408.1; 252/372; 422/5; 422/88; 422/103; 424/2; 424/76; 436/9; 422/123
[58] Field of Search ...................... 252/408, 372, 408.1; 23/230 R, 230 B, 232 R, 907; 73/19, 23, 1 G; 422/5, 123, 88, 99, 102, 103; 424/76, 2; 436/9; 53/97, 79

[56] References Cited

U.S. PATENT DOCUMENTS

| | | | |
|---|---|---|---|
| 3,595,607 | 7/1971 | Gores | 422/122 |
| 3,854,319 | 12/1974 | Burroughs et al. | 23/232 R |
| 3,951,855 | 4/1976 | Principe et al. | 252/408 |
| 3,997,296 | 12/1976 | Miller | 23/232 R |
| 4,003,257 | 1/1977 | Fletcher et al. | 23/232 R |
| 4,080,170 | 3/1978 | Borkenstein | 23/232 R |
| 4,146,566 | 3/1979 | Gaiser | 422/122 |
| 4,277,251 | 7/1981 | Leichnitz | 23/232 R |

FOREIGN PATENT DOCUMENTS

47860 3/1982 European Pat. Off. ............ 252/408

Primary Examiner—Teddy S. Gron

[57] ABSTRACT

A method and apparatus for precise control of vapor phase concentrations of volatile organic compounds is provided which utilize desorption of monolayers of the organic compound from a solid adsorbent. The method and apparatus can be used for measuring human olfactory system performance, for calibration of analytical chemical instruments, and in other applications.

14 Claims, 4 Drawing Figures

METHOD AND APPARATUS FOR PRECISE CONTROL OF VAPOR PHASE CONCENTRATIONS OF VOLATILE ORGANICS

BACKGROUND AND PRIOR ART

At present there is no accepted and easily used method for measuring human olfactory system performance. As a result, there is no way to determine whether this performance has changed as a result of exposure to environmental chemicals, sickness, medical treatments, age, or other unknown causes. Odor dilutions could be used for such testing, but no satisfactory method for preparing such dilutions is known.

In the past odor dilutions have been prepared either by mixing odorous vapors with odorless gases or by mixing odorous substances in liquid solutions in a solvent which was as close to being odorless as possible. These methods are cumbersome, difficult to accomplish accurately due to surface adsorption effects and slow diffusion times, difficult to verify by quantitive assay since the mixing apparatus or solutions must be transported to the assay facility. In the case of liquid dilutions, the near impossibility of finding a solvent suitable for non-polar substances (which constitute the majority of odorous substances) which is odorless and which has a known molecular composition has been severely limiting. The vapor-phase dilution system is limiting because it does not allow easy use of low concentrations of materials due to the limitations of gas flow metering systems. To achieve low concentrations, liquid dilutions are required with their attendant limitations.

SUMMARY OF INVENTION

The method of the present invention takes advantage of the fact that the equilibrium concentration of vapor over a solid onto which a volatile liquid is adsorbed is a monotonic function of the vapor pressure of the liquid, the affinity of the solid for the liquid, and the fraction of the solid surface area covered by the liquid monolayer. The simplest adsorption process, that which follows first order kinetics, is described by the Langmuir adsorption isotherm. The concentration of the vapor in the headspace over the solid adsorbent can be varied over a range of several orders of magnitude by appropriate selection of the solid phase and of the amount of volatile liquid added. As applied to precision olfactometry, for example, since the adsorbent selected will have a large ratio of surface area to mass, many head space vapor samples (sniffs) can be removed without significant change in the surface coverage fraction. With a large surface area, head space vapor equilibrium concentration is rapidly re-established following a sniff.

In one embodiment of the present invention, a single odor source (e.g. a volatile odorous organic compound) is prepared by mixing a measured amount of the odorous substance with a standard weight of adsorbent. The mixture is placed in a closed vessel and allowed to stand until an equilibrium distribution is achieved. For substances which are heat stable, the process can be accelerated by raising the temperature. The concentration of the head space vapor can be established with the use of a chromatographic detector of the flame or photoionization type. A sample of saturated headspace vapor over the pure odorous substance is used as the reference point. Concentrations below the sensitivity limits of the detector can be extrapolated because the desorption process is ideal at small surface coverage fractions. The head space vapor concentration will depend only upon temperature. Errors in vapor phase concentrations due to desorption from the interior surfaces of the olfactometer are minimized by the large ratio of solid adsorbent surface to vessel surface area.

There is a wide variety of adsorbing materials available. High energy surfaces include the activated carbons which have highest affinities for non-polar substances and silica gels which have highest affinities for polar substances. Useful lower energy surfaces are those commonly used as column packings for gas chromatography. Selection of the adsorbent will depend upon the chemical affinity and reactivity of the odorous substance and the desired vapor concentration range. High energy surfaces will catalyze oxidation, isomerization, and polymerization reactions. Dry air or nitrogen must be used to replace the headspace after a sniff due to the affinity of many adsorbing materials for water vapor.

Olfactometers based upon the monolayer desorption process have several advantages. There is no solvent and therefore no odor added by it. A wide range of intensities is easily realized. This is particularly significant when very low odor concentrations are desired. Equilibrium vapor concentration depends only upon temperature. Therefore inaccuracies due to capillary resistance, flow meter jitter, pressure and flow rate regulation, and valve setting repeatibility are eliminated. Because of the large surface area, vapor phase equilibrium is rapidly established.

The method and apparatus of this invention are also applicable to calibration of instruments, such as chromatographic apparatus. Using the principles described above, a gas sample is generated of predetermined concentration of the vaporized organic compound. This sample is passed through the analytical instrument for calibration purposes. The precise control of the vapor phase concentration provides a simple and highly accurate calibration reference.

BRIEF DESCRIPTION OF DRAWINGS

The present invention in its method of apparatus aspects are illustrated by the accompanying drawings, in which.

DETAILED DESCRIPTION

The present invention can be practiced with any organic compound which is in a liquid or solid state at the temperature at which the method is to be practiced, viz. ordinary room temperatures (20°–30° C.). The liquid or solid odor substance will have a significant vapor pressure, thereby evaporating or subliming the transfer of the substance to a gas (e.g., air) with which the substance is in contact. Most odor substances of interest for olfactory testing are organic compounds, being either in the liquid or solid phase at 25° C. Similarly, analysis of gases by chromatographic instruments and other gas analyzers are largely directed to determining concentrations of organic compounds. With respect to the volatile organic compounds to be used, therefore, this invention is of broad scope.

A wide variety of solid granular adsorbents can be used in practicing the invention. The usable adsorbents are those which provide adsorptive surfaces which have an affinity for the liquid or solid substance to be adsorbed. For example, such well known adsorbents as silica gels and activated carbons can be used. In general, activated carbons are preferred for adsorption of non-polar odor substances, since they have a higher affinity for such substances than for those which are polar in nature. Similarly, silica gels are preferred for polar odor substances since they have a higher affinity for these substances. Other examples of usable adsorbents include the following: graphitized carbons such as Carbopack; porous polymers such as Poropack and the Chromosorb 100 series of materials; or diatomaceous earth (which may be treated with sodium carbonate or other chemicals to modify the adsorption properties) coated with silicone oil, stearic acid, oxydipropionitrile, diethyl formamide, chlorooctadecanone, squalene, carbowax, a variety of polyesters, or Apiezon. It will be understood that the adsorbent should be selected so that it does not react chemically with the organic substance, and so that both the organic substance and the adsorbent remain stable.

By utilizing a volatile organic compound and an adsorbent of the character described, reproducible predetermined concentrations of the organic can be provided in gas carrier samples by the method of this invention. The organic such as an odor substance is applied to the solid granular adsorbent to partially coat its adsorptive surfaces. When the adsorptive surfaces are fully coated with a monomolecular layer of the organic, a condition is reached in which a gas in contact with the adsorbent will have the same concentration of the organic compound at equilibrium as where it is in contact with the organic in free liquid or solid form. As the amount of the organic is increased to provide a thicker coating on the adsorbent, the concentration of the organic in the gas at equilibrium remains constant for a given temperature. Therefore, in accordance with the present invention it is important that the amount of the organic compound on the adsorbent is limited to less than the minimum amount capable of saturating a gas in contact therewith, such as at a reference temperature of 25° C. This assures that the surfaces of the adsorbent are only partially coated. With this condition, the concentration of the organic in the vapor over the adsorbent for a given organic and a given adsorbent varies in relation to the fraction of the solid surface area of the adsorbent covered by the organic compound. Further, where the adsorbent provides a large ratio of surface area to mass, many headspace vapor samples (viz. sniffs) can be delivered without appreciable change in vapor concentration. Also, because of the large surface area, headspace vapor equilibrium concentration is rapidly re-established following a sniff.

While the amount of the organic on the adsorbent can be varied selectively, as desired, over a broad range from concentrations at the lower limits of detectibility up to full saturation, there are advantages in using low concentrations, such as an amount of odor substance on the adsorbent of less than 10% of the minimum amount capable of saturating a gas in contact therewith at an ambient temperature, viz. 25° C. In determining the required amount of the organic compound on an adsorbent to provide a predetermined concentration of the organic in a gas carrier, such low concentrations permit the measurement and plotting of the gas phase versus adsorbent concentration with greater accuracy and with less measurements. Further, as the amount of the organic on the adsorbent is decreased, measurements can be obtained in a linear relation region which can establish a basis for extrapolation of the measured values to concentrations below detectibility limits. Therefore, for certain purposes, it may be preferred to utilize an amount of the organic compound, such as an odor substance, on the adsorbent less than 1.0% of the minimum amount capable of saturating a gas in contact therewith at 25° C.

Where the organic compound is a liquid, a measured amount can be mixed with the solid granular adsorbent and the adsorbent held in an enclosed space until the liquid has become uniformly distributed on the adsorptive surfaces. A hold period of 24 hours at a temperature of 20° to 30° C. is usually sufficient to assure uniform distribution. Where needed, the desired uniform distribution can be promoted by using higher temperatures. This procedure is particularly helpful, where an odor substance or other organic is being applied which is normally solid at room temperatures. For example, a solid organic compound can be heated until it becomes a liquid, mixed with the adsorbent, and held at a temperature in which it remains in the liquid phase until it has become uniformly distributed on the adsorbent. If desired, solvent solutions can be used to apply the organic compound, but this is usually not necessary, and may be undesirable since most solvents are not totally odorless and the solvent will be adsorbed by the adsorbent.

After the organic has been applied to the adsorbent, as described above, the adsorbent is introduced into an enclosed space from which gas samples can be selectively removed. The enclosed space will contain a suitable gas such as an odorless gas in contact with the adsorbent. The adsorbent in maintained in contact with the gas until an adsorption-desorption equilibrium is reached so that the gas at a given temperature contains a given concentration of the organic. Thereafter, a gas sample can be removed from the enclosed space which will have a predetermined and reproducible concentration of the organic. For olfactometry, the gas volume in the enclosed space (the headspace) preferably has a greater volume than the amount of gas required for one sniff by a human subject. This will vary between adults and children. For example, from 20 to 40 cc. may be required for a sniff by an adult, while as little as 10 cc. is needed for a child. For general purpose olfactometry use, therefore, the headspace or gas volume should be greater than 50 cc., and will usually be several times this amount, such as 100 to 200 cc. or greater.

In general, human subjects are unable to discriminate differences in odor concentration which vary by factors of less than 10%. Therefore, even if the amount of odor substance withdrawn in each sample is 0.1% of the amount contained on the adsorbent, a number of samples can be withdrawn which are substantially identical with respect to olfactory response. However, it is preferred to limit the amount of the odor substance withdrawn in each gas sample to amounts which permit 1000 or more samples to be withdrawn before the concentration is reduced by a factor of 10%. Therefore, in general, it is preferred that the withdrawn gas sample should contain an amount of the odor substance less than 0.01% of the amount adsorbed on the adsorbent. This permits a plurality of substantially identical odor samples to be removed as required from the enclosed space, for example, from 1 to 1000 odor samples. Where a greater number of substantially identical volume samples are withdrawn, the amount of odor substance on the adsorbent in relation to the amount removed per sample will decrease linearly and the true concentration in any given sample can be determined by measuring the concentration in air of the vapor at the onset of the series and at the end of the series. To permit very large numbers of substantially identical odor samples to be removed, such as 10,000 odor samples, the amount of odor substance and adsorbent in the cartridge can be increased.

OLFACTOMETER APPARATUS

Figure 2:
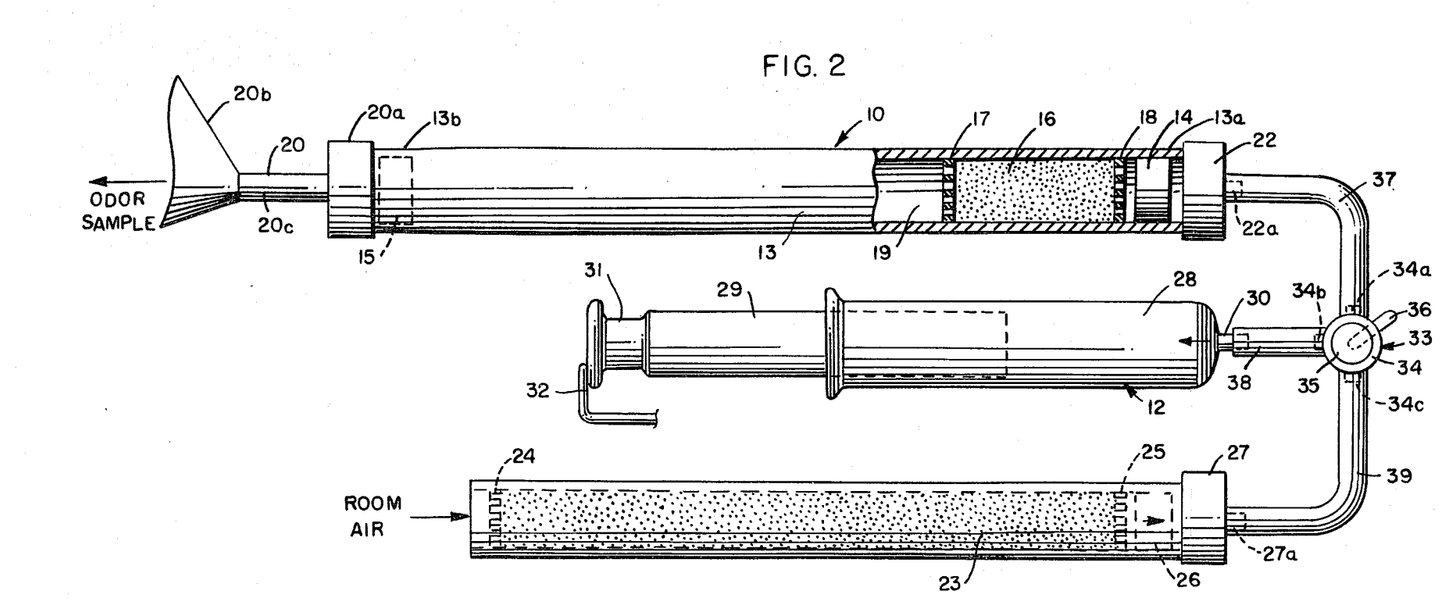
FIG. 2 is a plan view of an olfactometer apparatus which may be used in measuring human olfactory system performance pursuant to the present invention.

In FIG. 2, there is shown an apparatus assembly for dispensing odor samples of reproducible predetermined odor concentration. It includes an odor cartridge (10), an air cleaner tube (11) and an operating syringe (12) with associated valving and connecting tubing, as will subsequently be described in detail. In general, for dispensing an odor sample, all that is required is a container with at least one opening to the space enclosed thereby, openable means for closing the opening to seal the container, and adsorbent having an odor substance adsorbed thereon within the container and an odorless gas therein in contact with the solid granular adsorbent. Preferably, for the reasons described above, the amount of the odor substance on the adsorbent is limited to less than 10 percent of the minimum amount capable of saturating the odorless gas at 25° C. When in condition for dispensing an odor sample, the gas in contact with the adsorbent will contain a substantially equilibrium concentration of the odor substance. For long term dispensing use, the dispensing assembly may be prepared so that the gas in contact with the odor substance contains less than 0.01% of the amount of the odor substance on the adsorbent.

In the embodiment shown in FIG. 2, the odor cartridge (10) is in the form of a tube (13) having an inlet end (13a) for admission of the odorless gas and an outlet end (13b) for discharge of the gas containing the odor substance. The inlet end (13a) is provided with an inlet check valve (14), and the end (13b) providing the outlet opening is equipped with an outlet check valve (15). The adsorbent (16) with the odor substance thereon is disposed within the tube (13) so that the odorless gas in flowing through the tube passes through the adsorbent. In the illustration given, the granular adsorbent is disposed between press-fit perforated discs (17 and 18) adjacent the inlet end (13a). The headspace (19) containing the gas with the odor substance therein at an equilibrium concentration is provided between the disc (17) and the outlet check valve (15).

Figure 3:
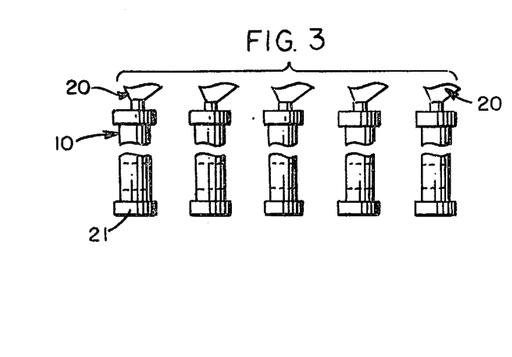
FIG. 3 is a plan view of a series of odor cartridges for use with the apparatus of FIG. 2.

To facilitate sniffing of a measured volume sample of the odor-containing gas, the outlet end (13b) is provided with a permanently attached nose cone (20) which has an attachment cap (20a) received on outlet end (13b) and a nose insertion portion (20b) connected by a tube (20c). Nose cone (20) may be molded from plastic as a unitary component, and slipped on to the outlet end of tube (13) and attached thereto by means of an adhesive. A series of such pre-assembled cartridges (10) is illustrated in FIG. 3. For example, each cartridge can contain a distinctly different concentration of the same odor substance, the gas concentration being determined by the amount of the odor substance applied to the adsorbent, as described above. The concentrations will usually differ by a factor of least 10% between the cartridges. For use of a selected cartridge, the slip-off cap (21) is removed from the inlet end, and the cartridge is inserted in the apparatus of FIG. 2 by slipping end (13a) into the slip on connector (22). Although the nose cones (20) may be made removable, it is preferred to have them permanently attached to the adsorbent-containing tubes (13) because the odor substance may remain in detectable amounts on the nose cone of the cartridge after use, which could interfere with subsequent testing, especially where the odor substance itself is changed. The nose cone material is preferably chosen to minimize adsorption of odors onto its surface.

The rest of the apparatus of FIG. 2 will now be described, it being understood that the illustrated components are not essential to the use of the odor cartridges (10). The air cleaner tube (11) contains a porous packing (23), which is provided within the tube between press-fit perforated discs (24 and 25). The packing (23) is prepared so that it will remove any odors from the room air and also substantially all of the moisture. For example, granules of silica gel and/or activated carbon may be mixed with granules of calcium chloride. By using the combination of silica gel and activated carbon, the complete removable of both polar and non-polar odors can be assured, while the calcium chloride and silica gel will adsorb the moisture. In a specific embodiment, these three ingredients may be combined in substantially equal parts by volume (viz. ⅓ silica gel, ⅓ activated carbon; and ⅓ $CaCl_2$).

The air cleaner tube (11) is also provided with an outlet check valve (26). The outlet end of the air cleaner tube (11) is received within slip off connector (27).

The syringe unit (12) consists of a hollow body member (28), a sliding plunger (29), a connector end portion (30), and an operating handle portion (31) on the plunger (29). There may also be provided an adjustable position stop member (32), which can be positioned to limit the amount of withdrawal of the plunger (29) from the body (28), as illustrated. As will be described, stop (32) in effect functions as a sniff volume limit.

A two-position control valve unit (33), which includes a fixed outer angular portion (34), and a rotatable inner cylindrical portion (35) connects to an operating handle (36). The ring portion (34) has three nipple extensions (34a, 34b, and 34c) connecting to and communicating respectively with conduit sections (37, 38, and 39). The other end of section (37) connects to a nipple extension (22a) of cartridge end connector (22), the other end of conduit section (38) to the syringe connector portions (30), and the other end of section (39) to a nipple extension (27a) of air cleaner connector cap (27).

Figure 2A:
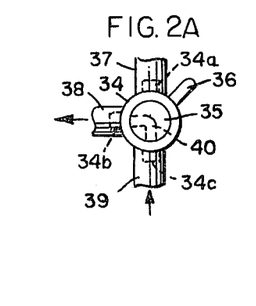
FIG. 2A is an enlarged detail view of the two-directional control value of the apparatus of FIG. 2 showing the valve in the air intake position.
Figure 2B:
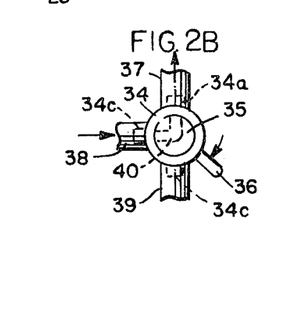
FIG. 2B is a view of the control value similar to FIG. 2A showing the valve in its odor discharge position.
Figure 2C:
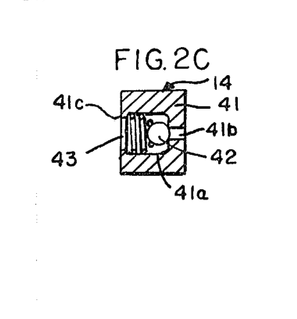
FIG. 2C is an enlarged cross-sectional view of the ball valve used in the apparatus of FIG. 1.

As shown in FIG. 2a, ring (34) internally provides gas flow passages (34a', 34b', and 34c') connecting respectively through nipples (34a, 34b, and 34c) with tubes (37, 38, and 39). Internally, valve cylinder (34) provides an L-shaped gas flow passage (40) which by means of handle (36) can be positioned, as shown in FIG. 2a to provide a passage communication between tubes (38 and 39). As shown in FIG. 2B, handle (36) can be moved downwardly to rotate cylinder (34) to align the L-shaped passage (40) with the passages communicating with tubes (37 and 38). The position of FIG. 2a is the air-intake position, while the position of FIG. 2b is the air-discharge position, as will be further described.

As already indicated, check valves (14 and 15) are provided at the ends of odor cartridge (10), and a check valve (26) is provided at the outlet end of air cleaner tube (11). The construction of these valves is illustrated in FIG. 2 for the inlet check valve (14). As shown, the valve body (41) provides a cavity (41a) with an inlet passage (41b), and spring retaining projections (41c). Within cavity (41a), there is positioned a ball (42) in sealing relation with either end of passage (41b) and the coil-spring (33) urging ball (42) into sealing position, the other end of the spring being held beneath projections (41c). The identical valve construction can be used as the outlet check valve (15) at the other end of cartridge (10). To function as the outlet check valve (26), the valve will be turned in the opposite direction so that the passage (41b) communicates with the interior of tube (11).

The sequence of operation of the apparatus of FIG. 2 will now be described. With control valve (33) in the loading position as shown in FIG. 2, plunger (29) is manually withdrawn until the outer end of handle (31) contacts stop (32), as illustrated in FIG. 2. This draws a measured amount of room air in through cleaner tube (11) and outlet check valve (26) into syringe body (28). The measured amount of air within syringe (28) is substantially odorless and of very low moisture content because of its passage through air clener tube (11). Valve operating handle (36) is then moved to the position shown in FIG. 2B so that passage (44) is aligned with the syringe connector tube (38) and the cartridge connector tube (37). Since the odorless gas within the headspace (13) of the cartridge contains an amount of the odor substance in equilibrium with the odor substance on the adsorbent (16), the apparatus is now ready for dispensing an odor sample of measured volume and predetermined odor concentration.

For the dispensing operation, the person using the apparatus, after exhaling air, places his nose inside of the adapter (20b) of the nose cone (20) and inhales. This will cause check valves (14 and 15) to open while check valve (26) remains closed. Plunger (29) will then move forwardly until it bottoms within syringe body (28). As this occurs, a volume of the odor-containing gas is withdrawn from headspace (13) into nose cone (20) corresponding with the volume of the air moving from syringe (28) into cartridge (10) through the adsorbent (16). As soon as the sniffing action is completed, check valves (14 and 15) close, and the equilibrium concentration of the odor substance in the gas within headspace (13) is rapidly restored. The cycle can then be repeated as required for dispensing additional odor samples of substantially identical volume and odor concentration.

In an alternate use of the apparatus of FIG. 2, a premeasured volume of the odor-containing gas can be dispensed by manually moving plunger (29) forwardly to force the air from syringe (28) into cartridge (10) with the dispensing of an equivalent amount of the odor-containing gas into and from nose cone (20). However, it will usually be preferred for the person whose sense of smell is being tested to operate the dispensing by an inhaling or sniffing action, the person taking a large enough sniff to remove all of the air from the syringe (28).

For obtaining an olfactory profile of the person being tested, a series of cartridges providing different concentrations of a particular odor can be successively inserted in the apparatus, and this process can be repeated with a number of different odor substances. Usually, the objective will be to find the lowest concentration of a particular odor substance that the person can detect.

INSTRUMENT CALIBRATION APPARATUS

Figure 4:
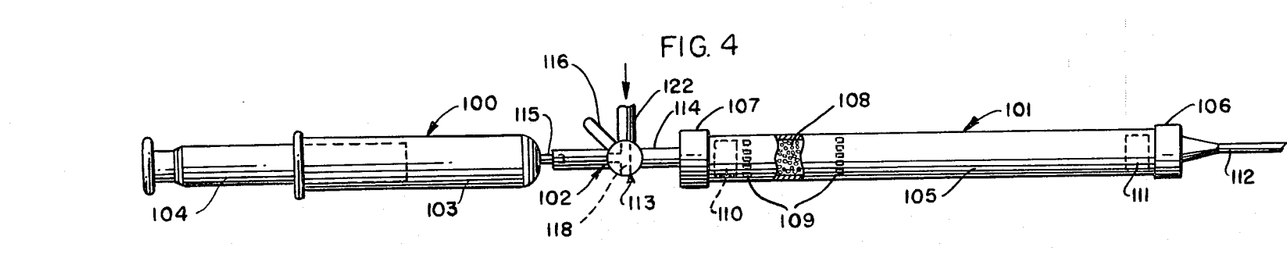
FIG. 4 is a plan view of an instrument calibration apparatus for use in applying the method of this invention to the calibration of gas analyzers.

In FIG. 4 there is shown an apparatus which can be used for preparing gas samples containing a predetermined concentration of an organic compound, the generated gas sample being introduced to a gas analyzer apparatus such as a chromatographic apparatus for use in calibrating the apparatus. The apparatus includes a gas sampling syringe (100), a gas dispensing cartridge (101) and a connecting tube assembly (102). The syringe includes a hollow tubular body (103) and a manually operable solid plunger (104) which is slidably received within the syringe tube (103). The cartridge includes a tubular barrel (105) with slip off end caps (106 and 107). Adjacent the inlet end portion of tube (105) there is provided a granular adsorbent (108) which is retained between perforated discs (109) in the manner similar to that described for odor cartridge (10). Also, there is provided an inlet check valve assembly (110) between the inlet to tube (105) and the adsorbent (108). Valve (110) is similar in construction to valve (14) of the apparatus of FIG. 2. Also, there is provided a similarly constructed outlet check valve (111) at the outlet end of tube (105). An opening in the end of cap (106) communicates with the hollow injection needle (112), and an opening in the end cap (107) communicates with the passage in tubular assembly (102).

Assembly (102) has a two position valve (113) interposed in the tubular portion (114) which extends between the hollow outlet projection (115) of syringe (100) and the inlet to cartridge (101). Valve (113) includes an operating handle (116) connected to a rotatable valve cylinder (117) providing a T-shaped passage (118) as shown more clearly in FIG. 4A, the body of valve (113) provides openings (119, 120, and 121). By rotating cylinder (117) by means of handle (116), the passages can be aligned in the loading position shown in FIG. 4 or in the discharge position shown in FIG. 4A. The operation of this apparatus will now be discribed in greater detail.

Figure 4A:
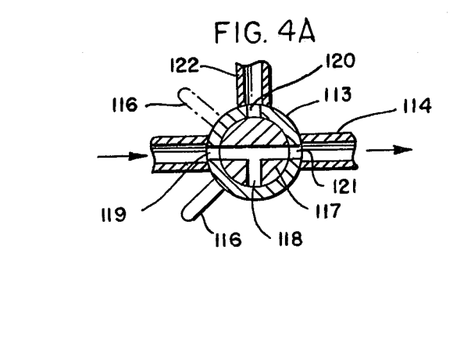
FIG. 4A is an enlarged cross-sectional detail view of the two-directional control valve of the apparatus of FIG. 4 showing the valve in discharge position.

With the valve (113) in the position shown in FIG. 4, a carrier gas such as nitrogen is supplied to tube (122) which communicates with opening (120) in the valve body and through the T-shaped passage (118) to the interior of syringe body (103). Then as plunger (104) is withdrawn, the syringe is filled with the carrier gas such as pure nitrogen gas. After the filling of the syringe, the setting of valve (113) is changed to the position shown in FIG. 4A in which the syringe (100) is connected to the cartridge (101). The injection needle (112) is then inserted through the septum on the inlet port of the instrument to be calibrated, and the syringe is emptied of the carrier gas by moving plunger (104)

inwardly. The dispensed carrier gas passes into cartridge (101) and through the adsorbent (108) containing the adsorbed organic compound to be used at a predetermined concentration for calibration of the instrument. As the syringe is emptied of the carrier gas, an equivalent amount of the gas carrying the predetermined concentration of the organic compound is forced into the headspace of the instrument being calibrated.

The method of this invention and its scientific basis are further illustrated by the following experimental examples

EXAMPLE I

Figure 1:
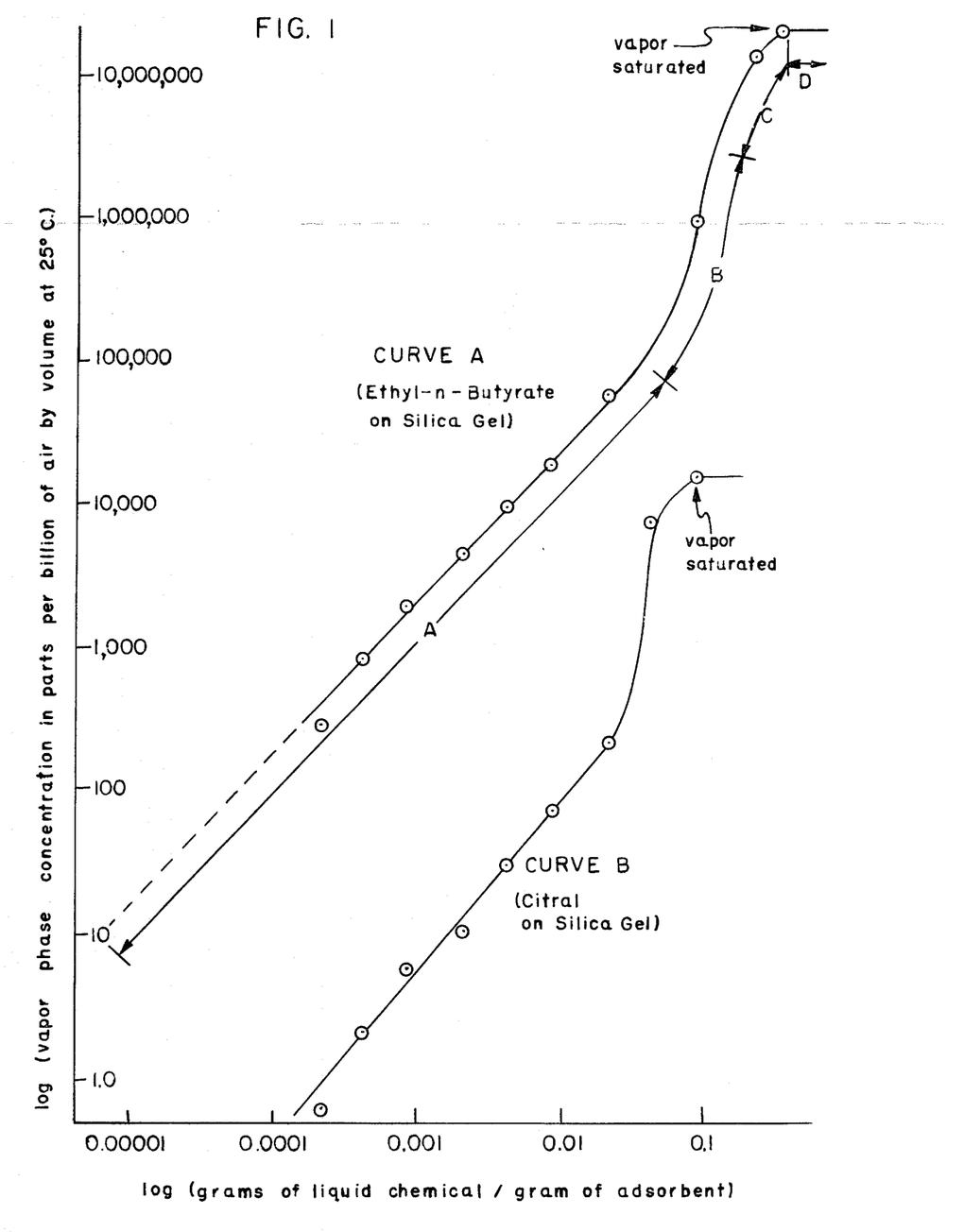
FIG. 1 is a graph on logarithmic coordinates illustrating the relationship between the amount of liquid organic compound (ethyl-n-butyrate or citral) on the solid adsorbent (silica gel) to the vapor phase concentration using liquid monolayer desorption in accordance with the method of the present invention.

FIG. 1 is a graph on logarithmic coordinates of the measured vapor concentrations in air over a solid silica gel substrate mixed with different amounts of liquid ethyl-n-butyrate and with liquid citral. Four regions on the ethyl-n-butyrate curve are marked. A is the linear region where the fraction of the solid surface covered $\theta$ is small and the vapor concentration is proportional to the fraction covered. B is the region where $\theta$ is not small compared to unity and the vapor concentration is proportional to $\theta/1-\theta$. C is the region where portions of the surface are covered by more than a single layer of ethyl-n-butyrate molecules. In this region the desorption process is complex and the vapor pressure must be determined by empirical measurement rather than by the theoretical equation. D is the region where the silica gel surface is completely covered by ethyl-n-butyrate. Here the system behaves as if it were a pure liquid with a large surface area and has a constant vapor pressure equal to the tabular value of saturated vapor pressure. Measured values are marked by dots within circles. The dashed portion of the line is the extrapolated vapor pressure at concentrations too low to be measured by available detection equipment.

To obtain the data plotted in FIG. 1, cartridges were prepared by adding the amounts of liquid ethyl-n-butyrate and of liquid citral tabulated below to 10 gram amounts of dry silica gel size 6 to 16 mesh. Each sample was placed in a tightly closed glass bottle with a Teflon plastic cap seal, agitated, and then allowed to reach equilibrium distribution by standing for 7 days. The concentration of the vapor in the headspace was then measured by placing the sample in a glass cartridge and displacing a small sample of the vapor from the cartridge with dry nitrogen, forcing the vapor sample into a vapor detector of the type known as a photo-ionization detector. The increase in electrical current through the detector which resulted from the presence of the vapor is a precise indication of the amount of vapor in the detector. The measured values of the electrical current in the detector and the equivalent vapor concentrations in parts per billion by volume at 25° C. are tabulated below. These are the values represented by the circle-enclosed dots in FIG. 1, and shown below in Tables A and B.

TABLE A

| | Ethyl-n-Butyrate on Silica Gel | | |
|---|---|---|---|
| Sample No. | Amt. of ethyl-n-butyrate added to 10 grams of silica gel | Measured detector current increase | Concentration of vapor in parts per billion by volume |
| 1 | 3.3 grams | 1.8 microamps | 21,000,000 |
| 2 | 2.2 grams | 1.4 microamps | 14,000,000 |
| 3 | 0.88 grams | 0.087 microamps | 1,000,000 |
| 4 | 0.44 grams | 9.0 nanoamps | 110,000 |
| 5 | 0.22 grams | 5.3 nanoamps | 61,000 |
| 6 | 0.088 grams | 1.7 nanoamps | 20,000 |
| 7 | 0.044 grams | 0.85 nanoamps | 9,900 |
| 8 | 0.022 grams | 0.40 nanoamps | 4,700 |
| 9 | 8.8 milligrams | 0.17 nanoamps | 1,980 |
| 10 | 4.4 milligrams | 0.075 nanoamps | 875 |
| 11 | 2.2 milligrams | 0.025 nanoamps | 290 |

TABLE B

| | Citral on Silica Gel | | |
|---|---|---|---|
| Sample No. | Amt. of citral added to 10 grams of silica gel | Measured detector current increase | Concentration of vapor in parts per billion by volume |
| 1 | 0.88 grams | 1.5 microamps | 16,000 |
| 2 | 0.44 grams | 0.75 microamps | 8,000 |
| 3 | 0.22 grams | 0.02 microamps | 213 |
| 4 | 0.089 grams | 7.0 nanoamps | 74.7 |
| 5 | 0.044 grams | 2.8 nanoamps | 29.9 |
| 6 | 0.022 grams | 0.98 nanoamps | 10.5 |
| 7 | 8.9 milligrams | 0.56 nanoamps | 5.97 |
| 8 | 4.4 milligrams | 0.20 nanoamps | 2.13 |
| 9 | 2.2 milligrams | 0.060 nanoamps | 0.64 |

EXAMPLE II

To prepare a series of odor test cartridges to measure human acuity to, for example, ethyl-n-butyrate vapor, the curve of FIG. 1 can be used to determine the amounts of ethyl-n-butyrate to be added per kilogram of silica gel to produce a graded series of samples at 20% vapor-concentration intervals. Table C below lists the amounts of liquid ethyl-n-butyrate added to each 1000 gram amount of silica gel and the resulting headspace vapor concentration in parts per billion by volume.

TABLE C

| Amount of Ethyl-n-Butyrate to be Used on Silica Gel to Obtain Predetermined Gas Concentration | |
|---|---|
| Grams (g) of ethyl-n-butyrate per kilogram of silica gel | Resulting vapor concentration in parts per billion (ppb) by volume |
| 59.3 grams | 160,000 ppb |
| 49.4 grams | 130,000 ppb |
| 41.2 grams | 108,000 ppb |
| 34.3 grams | 88,000 ppb |
| 28.6 grams | 71,000 ppb |
| 23.8 grams | 59,000 ppb |
| 19.9 grams | 49,000 ppb |
| 16.6 grams | 40,000 ppb |
| 13.8 grams | 33,000 ppb |
| 11.5 grams | 27,000 ppb |
| 9.58 grams | 22,000 ppb |
| 7.99 grams | 18,000 ppb |
| 6.66 grams | 15,000 ppb |
| 5.55 grams | 12,300 ppb |
| 4.62 grams | 10,000 ppb |
| 3.85 grams | 8,400 ppb |
| 3.21 grams | 6,900 ppb |
| 2.67 grams | 5,700 ppb |
| 2.23 grams | 4,750 ppb |
| 1.86 grams | 3,900 ppb |
| 1.55 grams | 3,200 ppb |
| 1.29 grams | 2,700 ppb |
| 1.07 grams | 2,200 ppb |
| 0.896 grams | 1,800 ppb |
| 0.746 grams | 1,500 ppb |
| 0.622 grams | 1,250 ppb |
| 0.518 grams | 1,050 ppb |

TABLE C-continued

Amount of Ethyl-n-Butyrate to be Used on Silica Gel to Obtain Predetermined Gas Concentration

| Grams (g) of ethyl-n-butyrate per kilogram of silica gel | Resulting vapor concentration in parts per billion (ppb) by volume |
|---|---|
| 0.432 grams | 870 ppb |
| 0.360 grams | 720 ppb |
| 0.300 grams | 600 ppb |
| 0.250 grams | 500 ppb |

EXAMPLE III

Since the adsorption-desorption process is ideal at low fractions of adsorbent surface coverage, samples can be prepared with vapor pressures accurately known at levels below the levels which can be verified by empirical measurement. The dashed portion of the ethyl-n-butyrate curve in FIG. 1 is an example of this. Available instrumental methods are not sensitive enough to measure vapor concentrations in the dashed portion of the line. However, the relationship between vapor concentration and amount of liquid added to the substrate is accurately linear in this region and therefore the vapor phase concentration is accurately predictable. Table D lists the amounts of ethyl-n-butyrate to be added to 1000 grams of silica gel adsorbent to prepare a series of vapor concentrations with 20% difference intervals in the range of 500 to 9 parts per billion of air by volume.

TABLE D

Amounts of Ethyl-n-Butyrate to be Added to 1000 Grams of Silica Gel to Provide Sample Series with 20% Concentration Intervals

| Grams (g) of ethyl-n-butyrate per kilogram of silica gel | Resulting vapor concentration in parts per billion (ppb) by volume |
|---|---|
| 0.250 grams | 500 ppb |
| 0.208 grams | 417 ppb |
| 0.173 grams | 348 ppb |
| 0.144 grams | 290 ppb |
| 0.120 grams | 242 ppb |
| 0.100 grams | 202 ppb |
| 0.083 grams | 168 ppb |
| 0.069 grams | 140 ppb |
| 0.058 grams | 117 ppb |
| 0.048 grams | 98 ppb |
| 0.040 grams | 82 ppb |
| 0.033 grams | 68 ppb |
| 0.028 grams | 57 ppb |
| 0.023 grams | 46 ppb |
| 0.0193 grams | 38 ppb |
| 0.0160 grams | 32 ppb |
| 0.0133 grams | 27 ppb |
| 0.0111 grams | 23 ppb |
| 0.0093 grams | 19 ppb |
| 0.0077 grams | 16 ppb |
| 0.0064 grams | 13 ppb |
| 0.0053 grams | 11 ppb |
| 0.0044 grams | 9 ppb |

EXAMPLE IV

To prepare cartridges containing vapors of substances which are solids at room temperature, the adsorbent is coated at elevated temperature. To do this, the adsorbent material and a measured amount of powdered, solid odorous material are shaken together in a closed container. The container is then placed in a water bath and held at a temperature a few degrees above the melting point of the odorous material for a period long enough to achieve uniform coating of the adsorbent. For example, if the odorous material is the synthetic musk, Exaltolide (which is 15-hydroxypentadecanoic acid lactone), the water bath can be at 40° C., which is 8 degrees above the melting point. One day in the water bath should be adequate to achieve uniform coating of the musk.

Examples of other odor substances which are solids at room temperature and which can be used in the method and apparatus of this invention include: 2-hexenoic acid, non-adecanoic acid, cinnamoyl chloride, stearic acid anhydride, cyclohexadecane, naphthalene, pentadecanal, coumarin, vanillin, indole, durene, diphenylamine, and mercaptobenzoic acid.

I claim:

1. The method of providing a predetermined concentration of a volatile organic compound in a gas carrier sample, comprising:
    (a) applying the volatile organic compound free of any other volatile compound to a solid granular adsorbent to partially coat its adsorptive surfaces, the amount of said compound on said adsorbent being less the minimum amount capable of saturating a gas in contact therewith at an ambient temperature, said compound and said adsorbent being chemically non-reactive;
    (b) introducing said organic compound-containing adsorbent into an enclosed space from which gas samples can be selectively removed, said enclosed space containing a carrier gas in contact with said adsorbent at said ambient temperature;
    (c) maintaining said adsorbent in contact with said gas until an adsorption-desorption equilibrium is reached so that said gas at said ambient temperature contains a predetermined concentration of said organic compound; and
    (d) removing a gas sample from said enclosed space containing said predetermined concentration of said organic compound.

2. The method of claim 1 in which the amount of said organic compound on said adsorbent is less than 10% of the minimum amount capable of saturating a gas in contact therewith at said ambient temperature.

3. The method of claim 1 in which a plurality of identical gas samples are removed from said enclosed space, the amount of said organic compound removed in each gas sample being less than 0.01% of the amount adsorbed on said adsorbent.

4. The method of claim 1 in which said adsorbent is silica gel.

5. The method of claim 1, or claim 2, or claim 3 in which said organic compound is an odor substance and said carrier gas is odorless, whereby said method can be used for dispensing odor samples.

6. The method of providing a predetermined concentration of a volatile organic compound in a gas carrier sample, comprising:
    (a) applying the volatile organic compound free of any other volatile compound to a solid granular adsorbent to partially coat its adsorptive surfaces, the amount of said organic compound on said adsorbent being limited to less than 10% of the minimum amount capable of saturating a gas in contact therewith at an ambient temperature, said compound and said absorbent being chemically non-reactive;
    (b) introducing said organic compound-containing adsorbent into an enclosed space from which gas samples can be selectively removed, said enclosed space containing a carrier gas in contact with said adsorbent at said ambient temperature;

(c) maintaining said adsorbent in contact with said gas until an adsorption-desorption equilibrium is reached so that said gas at said ambient temperature contains a predetermined concentration of said odor substance; and (d) removing a plurality of gas samples from said enclosed space with said organic compound therein, each of said gas samples containing an amount of said organic compound less than 0.01% of the amount initially adsorbed on said adsorbent, whereby a large number of samples of the same concentration can be removed from said enclosed space.

7. The method of claim 6 in which the amount of said organic compound on said adsorbent is less than 1.0% of the minimum amount capable of saturating said gas in contact therewith at said ambient temperature.

8. The method of claim 6 or claim 7 in which the adsorbent is silica gel.

9. The method of claim 6 or claim 7 in which said organic compound is an odor substance and said carrier gas is odorless, whereby said method can be used for dispensing odor samples.

10. An assembly for dispensing gas samples containing a reproducible predetermined concentration of a volatile organic compound, comprising a container with at least one opening to the space enclosed thereby, openable means for closing said opening to seal said container, said space containing a carrier gas in contact with a solid granular adsorbent having a volatile organic compound adsorbed thereon, said organic compound on said adsorbent being free of any other volatile compound and said organic compound and said adsorbent being chemically non-reactive, the amount of said organic compound on said adsorbent being less than 10% of the minimum amount capable of saturating said carrier gas at 25° C., said gas containing a substantially equilibrium concentration of said organic compound.

11. The assembly of claim 10 in which the said gas in said container contains less than 0.01% of the amount of said odor substance on said adsorbent.

12. The assembly of claim 10 or claim 11 in which said container is in the form of a tube having an inlet at one end for admission of said odorless gas and an outlet at the other end for discharge of gas containing said odor substance, said inlet opening being provided with inlet check valve means, and said outlet opening being provided with outlet check valve means, and said adsorbent being disposed within said tube so that said gas in flowing through said tube passes through said adsorbent.

13. The assembly of claim 12 in which said outlet opening for said gas sample is connected to a nose adapter to facilitate sniffing of said gas samples, where said assembly can be used with odorous organic compounds as an olfactometer.

14. The assembly of claim 12 in which said outlet opening for said gas sample is connected to an injector for introducing said sample into a gas analyzer instrument, whereby said assembly can be used to calibrate said instrument for response to said organic compound.

* * * * *